United States Patent
Carthey et al.

(10) Patent No.: US 12,065,393 B2
(45) Date of Patent: Aug. 20, 2024

(54) GOLD CONTAINING CATALYST, METHOD OF PREPARATION AND USE

(71) Applicant: JOHNSON MATTHEY PUBLIC LIMITED COMPANY, London (GB)

(72) Inventors: Nicholas Carthey, Reading (GB); Peter Johnston, Royston (GB)

(73) Assignee: JOHNSON MATTHEY PUBLIC LIMITED COMPANY, London (GB)

( * ) Notice: Subject to any disclaimer, the term of this patent is extended or adjusted under 35 U.S.C. 154(b) by 443 days.

(21) Appl. No.: 17/594,403

(22) PCT Filed: Jun. 19, 2020

(86) PCT No.: PCT/GB2020/051484
§ 371 (c)(1),
(2) Date: Oct. 14, 2021

(87) PCT Pub. No.: WO2020/254817
PCT Pub. Date: Dec. 24, 2020

(65) Prior Publication Data
US 2022/0194880 A1    Jun. 23, 2022

(30) Foreign Application Priority Data
Jun. 20, 2019   (GB) ..................... 1908844

(51) Int. Cl.
| | | |
|---|---|---|
| *C07C 17/08* | (2006.01) |
| *B01J 21/18* | (2006.01) |
| *B01J 31/22* | (2006.01) |
| *B01J 37/02* | (2006.01) |
| *B01J 37/04* | (2006.01) |

(52) U.S. Cl.
CPC .............. *C07C 17/08* (2013.01); *B01J 21/185* (2013.01); *B01J 31/226* (2013.01); *B01J 37/0213* (2013.01); *B01J 37/04* (2013.01); *B01J 2231/32* (2013.01); *B01J 2531/18* (2013.01)

(58) Field of Classification Search
CPC ......... C07C 17/08; C07C 17/06; C07C 17/02; B01J 21/185; B01J 31/226; B01J 37/0213; B01J 37/04; B01J 2231/32; B01J 2531/18; B01J 21/18; B01J 37/0203
See application file for complete search history.

(56) References Cited

U.S. PATENT DOCUMENTS

| 9,409,161 B2 | 8/2016 | Bishop et al. |
| 10,239,803 B2 | 3/2019 | Carthey et al. |
| 2019/0177251 A1 | 6/2019 | Carthey et al. |

FOREIGN PATENT DOCUMENTS

| CN | 103316704 A | 9/2013 |
| CN | 108126721 A | 6/2018 |
| EA | 201792587 A1 | 4/2018 |
| GB | 2492888 A | 1/2013 |
| GB | 2492888 B | 2/2016 |
| WO | 2013/008004 A2 | 1/2013 |

*Primary Examiner* — Jafar F Parsa
(74) *Attorney, Agent, or Firm* — BakerHostetler (57) ABSTRACT

The present invention relates to improvements in known gold containing catalysts. In particular, the present invention relates to improving the stability and/or inhibition of deactivation of gold containing catalysts via the addition of an inorganic oxide, hydroxide, oxo-salt or oxo-acid. There is also disclosed a method for preparing said catalyst most suitably via an impregnation method. Such catalysts are useful in the production of vinyl chloride monomer.

11 Claims, 6 Drawing Sheets

GOLD CONTAINING CATALYST, METHOD OF PREPARATION AND USE

FIELD OF THE INVENTION

The present invention relates to providing an improved gold containing catalyst, and a method of preparation of the same. In particular, but not exclusively, the present invention relates to improving the stability and/or inhibition of deactivation of gold containing catalysts via the addition of an additive selected from an inorganic oxide, hydroxide, oxo-salt or oxo-acid, and processes for preparing the same, and their use in manufacturing vinyl chloride monomer (VCM).

BACKGROUND

Known commercial processes for manufacturing vinyl chloride monomer (VCM) may combine ethylene, hydrogen chloride (HCl) and oxygen in the presence of copper chloride to form ethylene dichloride, which is decomposed at high temperature to form VCM and HCl. In an alternative commercial process, ethyne (acetylene) from carbide is reacted with HCl over a mercury-based catalyst. This process is preferred where there is access to cheap ethyne via carbide from abundant coal resources. The mercury catalyst, usually 8-10% mercuric chloride on activated carbon, used in this process is highly toxic. Such toxicity creates problems arising from handling during manufacture of the catalyst as well as during loading of catalyst and removing catalyst after a production campaign. A production campaign is generally of a six-month duration. Deactivation of the mercury catalyst and loss of $HgCl_2$ by sublimation or volatilisation from the reactor in use can lead to significant problems. The ethyne process using a mercury-based catalyst requires a lower capital investment than the ethylene process. If a non-volatile and less toxic catalyst could replace the mercury catalyst without requiring significant plant alterations in existing plant designs, this would be a significant advantage.

WO2013/008004, the teaching of which is herein incorporated in its entirety, describes a catalyst with improved toxicity compared to earlier VCM catalysts, which could be used in a catalysed process for the production of VCM from ethyne. However, the commercial up-take of such a catalyst has been hampered due to the cost of the gold required to manufacture the active catalyst. When relatively low levels of gold content are employed (to avoid high production costs), the stability of the catalyst is detrimentally affected, and catalytic activity is reduced. Furthermore, when manufacturing such gold containing catalysts it has been found that gold nanoparticles typically form, which in turn can result in the formation of carbon nanotubes during use of the catalyst, which subsequently leads to dusting from the catalyst resulting in loss of gold and deactivation of the catalyst. Therefore, there exists a need to provide gold containing catalysts with relatively lower content levels of the costly gold active material, but which do not exhibit undesirable reductions in catalyst stability, activity or selectivity, and preferably where gold nanoparticle formation is reduced or negated to avoid the formation of carbon nanotubes in use.

Preferred embodiments of the present invention seek to overcome one or more of the above disadvantages of the prior art. In particular, preferred embodiments of the present invention seek to provide improved gold containing catalysts via the addition of an inorganic oxide, hydroxide, oxo-salt or oxo-acid, and the methods of manufacturing such an improved catalyst, and its use in a chemical process for manufacturing vinyl chloride monomer (VCM) from acetylene are herein described.

SUMMARY OF INVENTION

According to a first aspect of the invention, there is provided a catalyst comprising:
  a complex of gold with a sulphur-containing ligand; and
  an additive selected from the group consisting of: an inorganic oxide, hydroxide, oxo-salt or oxo-acid; on a support.

According to a second aspect of the invention, there is provided a method of manufacturing said catalyst wherein,
  i) a solution of gold is provided,
  ii) a solution of sulphur containing ligand is provided,
  iii) a solution of an additive or precursor thereof is provided,
  iv) the gold solution is mixed with the sulphur containing ligand solution to provide a gold complex impregnation solution, and
  v-i) a catalyst support is impregnated with the gold complex impregnation solution, followed by drying the impregnated support, then impregnated with the solution from (iii), followed by drying the impregnated support, or
  v-ii) a catalyst support is impregnated with the solution from step (iii), followed by drying the impregnated support, then impregnated with the gold complex impregnation solution, followed by drying the impregnated support.

According to a third aspect of the invention, there is provided an alternative method of manufacturing said catalyst characterised in that,
  i) an impregnation solution is provided comprising a gold complex and an additive or a precursor thereof;
  ii) a catalyst support is impregnated with the solution from step (i) to produce an impregnated support, followed by drying the impregnated support.

According to a fourth aspect of the invention, there is provided a process for the hydrochlorination of an alkyne comprising reacting said alkyne with HCl in the presence of a catalyst according to the first aspect of the invention.

Herein all % relate to percentages by weight of the total catalyst weight, unless otherwise stated.

DETAILED DESCRIPTION

Catalyst

In the catalyst of the invention, the active catalytic species comprises gold (Au) in a positive oxidation state, preferably as $Au^{3+}$ and $Au^{1+}$, although some of the gold present may be in the form of metallic gold ($Au^0$). In some embodiments of the invention, the catalysts may be considered to comprise gold particles having a core comprising metallic gold and a shell or surface layer comprising higher oxidation state gold species including $Au^{3+}$. The shell need not be complete, but preferably all or substantially all the exposed surface of the particle has the surface higher oxidation state gold species; for example, if the metallic gold is partially surrounded by support, the "shell" may extend only over the exposed particle surface. $Au^{3+}$ need not be the only higher oxidation state gold species present in the shell, and $Au^{1+}$ may also be present, for example. Such higher oxidation state species may be stabilised by halide, for example in prior art catalysts. It has been widely proposed in the prior art that the higher oxidation state gold species are the active species for catalysing the reaction of acetylene with HCl. It is believed that in the catalysts of the present invention, the gold is stabilised in a higher oxidation state by complexation with sulphur-containing ligands. The core of the particles typically comprises metallic gold ($Au^0$) but alternative gold species may also be present in the core.

As used herein, the term "additive" means an inorganic oxide, hydroxide, oxo-salt or oxo-acid. Herein, "inorganic" means not containing carbon. As used herein the term "additive precursor" means a material which can be converted into an inorganic oxide, hydroxide, oxo-salt or oxo-acid, typically following hydrolysis and/or drying. Additive precursors may or may not contain carbon.

As will be described further below, the methods of the invention prepare a catalyst by impregnating the catalyst support with an additive or additive precursor. Without wishing to be bound by theory, it is thought that the additive or additive precursor forms at least a partial layer around the gold particles. Following hydrolysis and/or drying, the result is generally a layer of inorganic oxide around the particles of gold complex, although the layer may include one or more of an inorganic oxide, hydroxide, oxo-salt or oxo-acid, depending on the method of preparation. It is thought that the presence of this layer prevents deactivation of the gold particles.

Suitably, the catalyst contains between 10 and 0.01% additive, preferably 10 and 0.1% additive, preferably between 5 and 0.1%, more preferably between 3 and 0.5%. Low levels of additive are preferred to avoid the level of additive having a negative effect on the activity of the catalyst, yet a sufficient amount of additive must be present to achieve the increase in stability of the catalyst, a level of between 5 and 0.1% additive has been found to achieve the best balance of these two requirements, although varying amounts of additive may be preferred depending on the salt or acid selected and the individual operating parameters of any process that the catalyst is used in. The additive may include a mixture of one or more of the inorganic oxide, hydroxide, oxo-salt or oxo-acid.

As used herein, an oxo-salt is a salt containing an anion of the formula $[M_xO_y]^{z-}$, where M is an element other than carbon or oxygen. Examples include metasilicate $[SiO_3]^{2-}$, orthosilicate $[SiO_4]^{4-}$, teraborate $[B_4O_7]^{2-}$ and phosphate $[PO_4]^{3-}$. An oxo-acid is the corresponding protonated form, e.g. $[PO_4]^{3-}$ and $H_3PO_4$, which in some instances may depolymerize e.g. $[B_4O_7]^{2-}$ and $B(OH)_3$. Preferred elements M include Zr, Ce, La, Y, Ti, Bi, Zn, Al, V, Cr, Mn, Mo, W, Re, B, N, Si, P, S, Ge, As, Se, Sn, Sb, Te, Cl, Br and I. More preferred elements M include Zr, Ce, La, B, Si, P and S.

In preferred embodiments the additive is:
(i) an oxide or hydroxide of a metallic, metalloid or non-metal element; or
(ii) an oxo-salt or oxo-acid of a metalloid or non-metal element.

Herein, a metalloid element is one selected from B, Si, Ge, As, Sb and Te; preferred metalloids are B and Si, especially Si. Preferred non-metals are S and P, especially P.

In a preferred embodiment the additive is an oxide, hydroxide, oxo-salt or oxo-acid of boron, silicon, sulfur or phosphorus, more preferably of boron, silicon or phosphorus, more preferably of boron or silicon. Typical contents of boron, silicon, sulfur or phosphorus will be 0.01-10 wt %, such as 0.1-10 wt %, such as 0.5-10 wt % or 0.5-5 wt %, based on the total weight of catalyst. The content of these elements may be measured by techniques known to those skilled in the art, such as inductively coupled plasma (ICP) techniques, which include ICP-MS, ICP-AES and ICP-OES.

In a preferred embodiment the additive is an oxide, hydroxide, oxo-salt or oxo-acid of silicon. The catalyst may include one or more silicon species, e.g. silicon dioxide, silicates, metasilicates etc. Typical silicon contents will be 0.01-10 wt %, such as 0.1-10 wt %, such as 0.5-10 wt % or 0.5-5 wt %, based on the total weight of catalyst. The content of silicon may be measured by techniques known to those skilled in the art, such as inductively coupled plasma (ICP) techniques, which include ICP-MS, ICP-AES and ICP-OES.

Advantageously, the additive should be stable, relatively low or non-reducing/oxidising oxide, hydroxide, oxo-salts or oxo-acids of metalloid or non-metallic elements. In some embodiments the additive or additive precursor is an alkali, alkaline or rare earth metal salt. Preferred counter-ions include ammonium or alkali metals, for example: ammonium silicate, ammonium borate, ammonium sulphate, ammonium phosphate, sodium silicate, sodium borate, sodium sulphate or sodium phosphate.

Particularly suitable inorganic oxo-acids are boric acids, phosphoric acid, silicic acids, or sulphuric acid. Boric acid ($B(OH)_3$) is a particularly preferred boron-containing oxo-acid.

More especially, the following additives have been found to be particularly useful: sodium metasilicate pentahydrate, sodium tetraborate, boric acid, and trisodium orthophosphate. In particular, the additive is preferably a sodium silicate salt, and most preferably is sodium metasilicate pentahydrate.

In some embodiments the additive may be the product derived from an additive precursor that forms a non-reducible inorganic oxide upon transformation (typically by thermal or chemical degradation, and suitably hydrolysis) following deposition onto a catalyst support; preferable inorganic oxides that may be formed in this way include $SiO_2$, $Al_2O_3$, $TiO_2$, $ZrO_2$, $La_2O_3$, $CeO_2$ their sub-oxides or mixtures thereof. The additive precursor may be inorganic or organic. Suitable inorganic and organic precursors will be appreciated by the skilled person, and would include alkoxides of the aforementioned elements, for example, tetraethylorthosilicate (TEOS), titanium isopropoxide and the like. Alternative precursors include metal salts such as metal chlorides or metal nitrates which are converted through hydrolysis to the corresponding hydroxides and oxides.

Typically the catalyst contains less than 1% of gold. Preferably the catalyst contains less than 0.5% of gold. Preferably the catalyst contains less than 0.1% of gold. More preferably the catalyst contains no more than 0.075% of gold, and most preferably the catalyst contains no more than 0.05% of gold. For some uses the catalyst may contain no more than 0.025% of gold without loss of commercially acceptable catalyst activity. Gold levels of less than 0.1% by weight of the catalyst can be considered to be low gold content catalysts, and atypical. The use of lower levels of gold are attractive due to the corresponding reduction in cost of manufacturing the catalyst as ordinarily the gold will be the most expensive component of the catalyst. However, hitherto, the ability to utilise these relatively low levels of gold (especially at levels of no more than 0.05%) have been limited due to the loss of stability of the catalyst product resulting in unacceptably low levels of catalyst activity, which is observed as unacceptably low product conversion levels. The incorporation of the additive in the catalyst has allowed the disadvantages associated with using relatively low levels of gold (no more than 0.05%) to be overcome. It is surprising that the addition of an additive has been found to be advantageous in the gold containing catalysts of the present invention.

Additionally, or alternatively, even in low gold containing catalysts with relatively high levels of gold content (i.e.

more than 0.05%) improvements are observed in the properties of the catalyst. More especially, nanotube formation had advantageously been inhibited. Therefore, the addition of an additive in gold containing catalysts containing relatively high levels of gold (i.e. more than 0.05%) has surprising benefits. Nanotube formation leads to deactivation of the catalyst, and hence the addition of an additive has been found to inhibit the deactivation of gold containing catalysts. The process of catalyst deactivation via nanotube formation occurs largely due to reduction of oxidized gold in the catalyst, and gold particle growth, forming relatively large (>200 nm) gold nanoparticles. It is also believed that the nanoparticles may also act as nuclei for the formation of carbon nanotubes. Nanotube formation manifests as a yellow powdery deposit on the catalyst pellets, leading to dust formation and loss of gold contained in this powder, resulting in deactivation of the catalyst.

Without wishing to be bound by theory, it may be that a thin film of additive or additive precursor is formed around the gold particles inhibiting sintering and nanotube nucleation. The additive precursor may undergo hydrolysis or partial hydrolysis to form its corresponding non-reducible oxide or sub-oxide around the gold particles; this may prevent migration and sintering of the gold particles of the catalyst upon/during use or act as a barrier between the carbon support and the metal particle.

Having consideration of the above paragraphs, the skilled person will appreciate that the benefits of inclusion of an additive in a gold containing catalyst, according to the present invention, are twofold: one, the stability of low gold containing catalysts (up to 0.05%) are improved, and loss of activity is negated, and two, inhibition of deactivation of gold containing catalysts generally is achieved, by limiting the formation of nanotubes on the catalyst surface.

Any known catalyst support may be used to make the catalyst of the invention. Typical metal oxide supports such as alumina, silica, zeolite, silica-alumina, titania or zirconia and composites thereof may be used.

Most preferably, the catalyst support is made from carbon, including carbon supports derived from natural sources (peat, wood, coal graphitic, etc or combinations thereof) or synthetic carbons. The carbon is preferably an activated carbon, activated for example by steam, acid, or otherwise chemically activated. Preferred carbon supports include a high surface area activated carbon, preferably of surface area greater than 800 m$^2$/g, such as a 1300 m$^2$/g carbon extrudate. Carbon extrudates are available as "high purity" or "ultra-high purity" grades commercially and such grades are typically acid washed to remove impurities. A combination of metal oxide and carbon may also be used as a catalyst support.

The catalyst support may take the form of powders, granulates or particles formed in various shapes, ("shaped units"). Preferred shaped units include spheres, tablets, cylinders, multi-lobed cylinders, rings, miniliths etc. or a massive catalyst unit such as a monolith. Alternatively, the catalyst in the form of a powder may be included in a coating formulation and coated onto a reactor wall or shaped substrate such as a monolith. One preferred form of catalyst support comprises a plurality of shaped units in the form of cylinders, spheres or lobed cylinders each having a diameter of 0.1-10 mm, or, more preferably a diameter in the range 1-3 mm. In the case of a cross-section shape having a non-uniform diameter, such as a lobed cylinder, the diameter is an average diameter. Such catalyst support shapes are commercially available and may be made by extrusion, tabletting or by other methods.

The sulphur may be present in the catalyst in the form of a sulphur compound containing sulphur in a reduced or oxidised state or a combination of reduced and oxidised states, for example as in the thiosulphate ion. More especially, the sulphur is present in a sulphur-containing compound which is a ligand capable of forming a complex with a gold species, or which is complexed with the gold species. More preferably, the sulphur-containing ligand is capable of stabilising gold in a positive oxidation state. Suitable sulphur-containing ligands are oxidising ligands, especially oxygen donating ligands, containing sulphur in a positive oxidation state, or sulphur-donating ligands. Preferred sulphur-containing compounds include sulphates, sulphonates, thiosulphates, thiocyanates, thioureas, thiols and thionyl chloride. Preferred thioureas include thiourea itself or substituted thioureas. Preferred thiols include thiopropionic acid and thiomalic acid.

In a preferred embodiment, the sulphur-containing compound is a ligand capable of forming a complex with a gold species through a sulphur atom, or which is complexed with the gold species through a sulphur atom. In this embodiment the ligand includes one or more sulphur atoms, at least one of which is sulphur-donating. Preferred sulphur-donating ligands include thiosulphates, thiocyanates, thioureas, thiols and thionyl chloride. Preferred thioureas include thiourea itself or substituted thioureas. Preferred thiols include thiopropionic acid and thiomalic acid.

The amount of sulphur in a fresh catalyst is preferably in the range from about 0.005-15% by weight, more preferably from 0.03 to 7% by weight in the dry catalyst, especially up to about 5% by weight. In one embodiment of the invention, in which the gold complex is a gold-thiosulphate complex, the mole ratio of S to Au in the complex is preferably in the range from about 3:1 to about 8:1. In such an embodiment containing a preferred amount of gold, the amount of sulphur in the catalyst may be in the range of 0.03 to 1.50% by weight. Some sulphur originating from sources other than the S-containing complex may also be present in the catalyst, for example incorporated in the support material.

The catalyst may additionally comprise a metal other than gold or any metal forming the support compound. Known promoters for use with gold catalysts used for hydrochlorination reactions include compounds of cobalt, copper or lanthanum and such metals may be present in the catalysts of the invention or the catalysts used in the process of the invention. Group 1 and Group 2 metals may also be advantageously incorporated in the catalysts of the invention. Therefore, the catalyst may comprise, in addition to gold, a metal or a compound of a metal selected from the group consisting of cobalt, copper, lanthanum, cerium, lithium, sodium, potassium, rubidium, caesium, magnesium, calcium, strontium and barium. The additional metal may be present as a promoter or may have another function in the catalyst or its preparation. For example, some metals, such as calcium, are believed to inhibit the formation of carbon deposits on the catalysts and can therefore be used to help maintain the activity of the catalyst over a period of time. Therefore, even if the presence of a metal does not increase the activity of a catalyst in the short-term it may be regarded as a promoter if it reduces the tendency of a catalyst to deactivate during its use in a reaction or has another beneficial effect on the practical use of the catalyst.

Manufacture of the Catalysts

According to a second aspect of the invention, there is provided a method of manufacturing a catalyst according to the first aspect of the invention wherein,
i) a solution of gold is provided, ii) a solution of sulphur containing ligand is provided, iii) a solution of an additive or precursor thereof is provided, iv) the gold solution is mixed with the sulphur containing ligand solution to provide a gold complex impregnation solution, and v-i) a catalyst support is impregnated with the gold complex impregnation solution, followed by drying the impregnated support, then impregnated with the solution from (iii), followed by drying the impregnated support, or v-ii) a catalyst support is impregnated with the solution from step (iii), followed by drying then impregnated support, then impregnated with the gold complex impregnation solution, followed by drying the impregnated support.

It is generally preferred to carry out the order of impregnations set out in v-i).

According to a third aspect of the invention, there is provided an alternative method of manufacturing a catalyst according to the first aspect of the invention wherein, i) an impregnation solution is provided comprising a gold complex and an additive or a precursor thereof;

ii) a catalyst support is impregnated with the solution from step (i) to produce an impregnated support, followed by drying the impregnated support.

This alternative method is preferred as it requires only one impregnation and drying step, providing a simpler and less costly catalyst preparation route.

In a preferred embodiment according to the third aspect of the invention, i) a solution of gold is provided, ii) a solution of sulphur-containing ligand is provided, iii) an additive or precursor thereof is added to either the solution of gold, or the solution of sulphur-containing ligand, prior to step iv), iv) the gold solution is mixed with the sulphur-containing ligand solution, wherein either the gold or sulphur-containing ligand solution also comprises the additive or precursor thereof, to provide an impregnation solution, v) a catalyst support is impregnated with the impregnation solution, followed by drying the impregnated support.

As provided by the method according to the third aspect of the invention, the additive or additive precursor may be added to either the solution of gold, or the solution of sulphur-containing ligand. Preferably the additive or additive precursor is added to the sulphur containing ligand solution where it would cause the gold to precipitate out of solution if added to the gold containing solution, and alternatively the additive or additive precursor is added to the gold containing solution where it would cause unfavourable reactions with the ligand if introduced to the ligand containing solution.

In some embodiments it is preferred that the pH of the solution of gold (prior to forming the gold complex) is neither too strongly acidic nor too strongly alkaline. Under strongly acidic conditions some sulphur-containing ligands are unstable, which is detrimental to formation of the gold complex and leads to unwanted impurities in the impregnation solution. For instance, thiosulphate is known to form the tetrathionate ion ($[S_4O_6]^{2-}$) under acidic conditions. Under strongly alkaline conditions the gold solution may form a colloid, which again is detrimental to gold complex formation. A preferred pH range for the solution of gold is pH 5-8, preferably pH 5.5-7.5. In a preferred embodiment the solution of gold is prepared by adjusting an aqueous solution of $HAuCl_4$ using a base such as NaOH or KOH.

According to an additional and alternative embodiment of the invention, there is provided a method of manufacturing said catalyst wherein the step of impregnating the catalyst support with the additive is achieved by providing an additive precursor and transforming the precursor to the inorganic oxide, hydroxide, oxo-salt or oxo-acid to result in the catalyst support being impregnated with the desirable additive, drying can then be performed as necessary. In this case, the catalyst support would be impregnated with the additive precursor and then the precursor would be transformed preferably by thermal or chemical degradation into the additive. This would result in the catalyst support being impregnated with the additive of choice.

In a method according to the second aspect of the invention, involving sequential impregnations of gold complex followed by an additive precursor, it is sometimes preferred to use a strongly alkaline solution of gold complex for the first impregnation step if the additive precursor is resistant to hydrolysis under neutral or mildly alkaline conditions. In this embodiment the pH of the impregnation solution containing the gold complex is preferably pH 9 or above, preferably pH 10 or above, more preferably pH 11 or above. The appropriate pH may be achieved by adding a base such as NaOH or KOH once the gold complex has been formed. Without wishing to be bound by any theory, the alkaline solution of gold complex used to impregnate the catalyst support is believed to basify the support and thereby precondition the support to hydrolyse the additive precursor in the subsequent impregnation step. This is particularly preferred when hydrolysis of the precursor is required to form the corresponding oxide, e.g. in the case where the inorganic precursor is a metal nitrate or chloride.

Catalysts may be prepared using a variety of catalyst preparation techniques known generally in the art, for example impregnation, preferably using incipient wetness methods, or by deposition-precipitation methods. In the methods of manufacturing a catalyst according to the invention the catalyst is preferably made by impregnating the support with a solution of a complex of gold with a sulphur-containing ligand, to form a gold complex, in combination with an additive or additive precursor. Preferred gold complexes are soluble in readily available solvents which present few environmental hazards. The preferred solvent is an organic solvent, water, or a mixture thereof. The solvent is preferably water. Preferred solutions for impregnation include aqueous solutions of gold sulphates, sulphonates, thiosulphates, thiocyanates, thiourea, thionyl chloride, thiopropionic acid and thiomalic acid.

In one preferred embodiment, the method of the invention comprises impregnating a particulate carbon support with an aqueous solution containing a complex comprising a compound of gold and a compound containing a thiosulphate ion, with an additive or additive precursor, followed, if necessary, by separation of excess solution and then drying the impregnated material.

It is preferred that the impregnation is carried out by the incipient wetness or "pore-filling" protocol, in which the amount of solution used is calculated to be just fill the pores of the support. Suitably, the compound of gold and compound containing a thiosulphate ion together form a gold-thiosulphate complex, and the additive has a stabilising effect on the gold containing complex formed. Typically, using an incipient wetness method of impregnation, the volume of impregnation solution used is 100%± up to about 20% of the measured (or calculated) pore volume of the support. The support is usually mixed with the impregnation solution by tumbling or the impregnation solution may be added, e.g. drop-wise or by spraying, to an agitated bed of support over a period of time. As an alternative, the catalyst support may be impregnated with the impregnation solution containing the gold complex and additive or additive precursor using an excess volume of impregnation solution so that the gold and/or sulphur-compound is deposited on the catalyst support by absorption or by ion-exchange reactions. The person skilled in the art of catalyst manufacture is acquainted with such methods of preparing catalysts by impregnation of support materials with a solution of active metal compounds.

The amount of the gold, sulphur and additive or additive precursor in the impregnation solution is calculated to provide the required amount of gold, sulphur and additive in the finished catalyst.

The impregnation solution containing the gold complex may contain an additional metal compound, for example including a compound of a metal selected from the group consisting of cobalt, copper, lanthanum, cerium, lithium, sodium, potassium, rubidium, caesium, magnesium, calcium, strontium and barium. The additional metal, if present, may alternatively be added to the catalyst in a separate step, for example by impregnating a gold-containing catalyst particle with a solution of a compound of the additional metal, or by impregnating a support material with such a solution before the solution containing the gold complex is added to the catalyst.

In an alternative, though less preferred, manufacturing process the catalyst may be prepared by known solid state processes, for example, by mixing dry support, gold, ligand, and additive or additive precursor components. In this case the gold-ligand complex may be pre-formed in an initial step. Ball milling is a particularly suited solid-state process method, however, more uniform application of active components to the catalyst support can be achieved via the support impregnation methods disclosed herein.

As stated above, preferably the catalyst support is carbon, and this may be subject to an acid wash, preferably using hydrochloric acid, nitric acid, phosphoric acid or sulphuric acid, which preferably may be carried out prior to impregnation with the gold complex containing impregnation solution. This may be done, for example, by dispersing the carbon in hydrochloric acid, optionally heating, possibly to boiling, draining, washing with distilled or deionised water and drying in air. As an alternative to using an acid wash procedure in the preparation of the catalyst a pre-treated or acid washed support may be obtained from a manufacturer of carbon supports as a commercial material when it is desired to use an acid-washed form of carbon support.

Optionally, the catalyst may require an activation step prior to use in a chemical process. In such cases, it may be more correct to refer to the dried, impregnated catalyst support as a catalyst precursor, but, for simplicity, we refer herein to such materials as catalysts, whether or not they require activation (or pre-activation) to attain their full catalytic activity.

Uses of the Catalyst

It is envisaged that the catalysts of the present invention will be useful in any chemical process where gold containing catalysts are known to find utility. However, a preferred chemical process of the invention comprises a process for the manufacture of vinyl chloride (also referred to as vinyl chloride monomer or VCM) by hydrochlorination of acetylene, comprising reacting acetylene with hydrogen chloride (HCl) in the presence of a catalyst comprising a complex of gold with a sulphur-containing ligand and an additive on a support. Preferably the catalyst is a catalyst according to the invention and/or made using a method of the invention. The process is carried out at elevated temperature, usually between about 100° C. and 250° C., more preferably <200° C. The HCl and acetylene are preferably premixed, and also preferably pre-heated to the reaction temperature. Normally HCl is present in excess of the amount required for the stoichiometric reaction. The catalyst may be present in the reactor in the form of a fixed bed of catalyst particles arranged such that the feed gases are passed over or through the catalyst bed. Alternative reactor arrangements may be used, including fluidised beds or other moving bed arrangements. The catalyst may alternatively be provided in the form of a monolith or coated on the wall of a reactor vessel. The catalyst bed may be provided with means to regulate the temperature, to avoid over-heating due to the exothermic reaction or to raise the temperature, if required. It may be preferred to treat the catalyst with HCl before use in the process. This treatment is typically carried out by flowing HCl over the catalyst for a period of at least an hour at a temperature of at least 50° C., more especially >100° C. This pre-treatment may take place in the reactor by operating with a flow of HCl without the acetylene, at a suitable temperature.

It will be appreciated that features described in relation to one aspect of the invention may be equally applicable in another aspect of the invention. For example, features described in relation to the catalyst of the invention, may be equally applicable to the catalyst prepared by the method of manufacturing of the present invention, and vice versa.

The invention will now be further described in the following examples with reference to the attached drawings, in which:—

EXAMPLES

Figure 1:
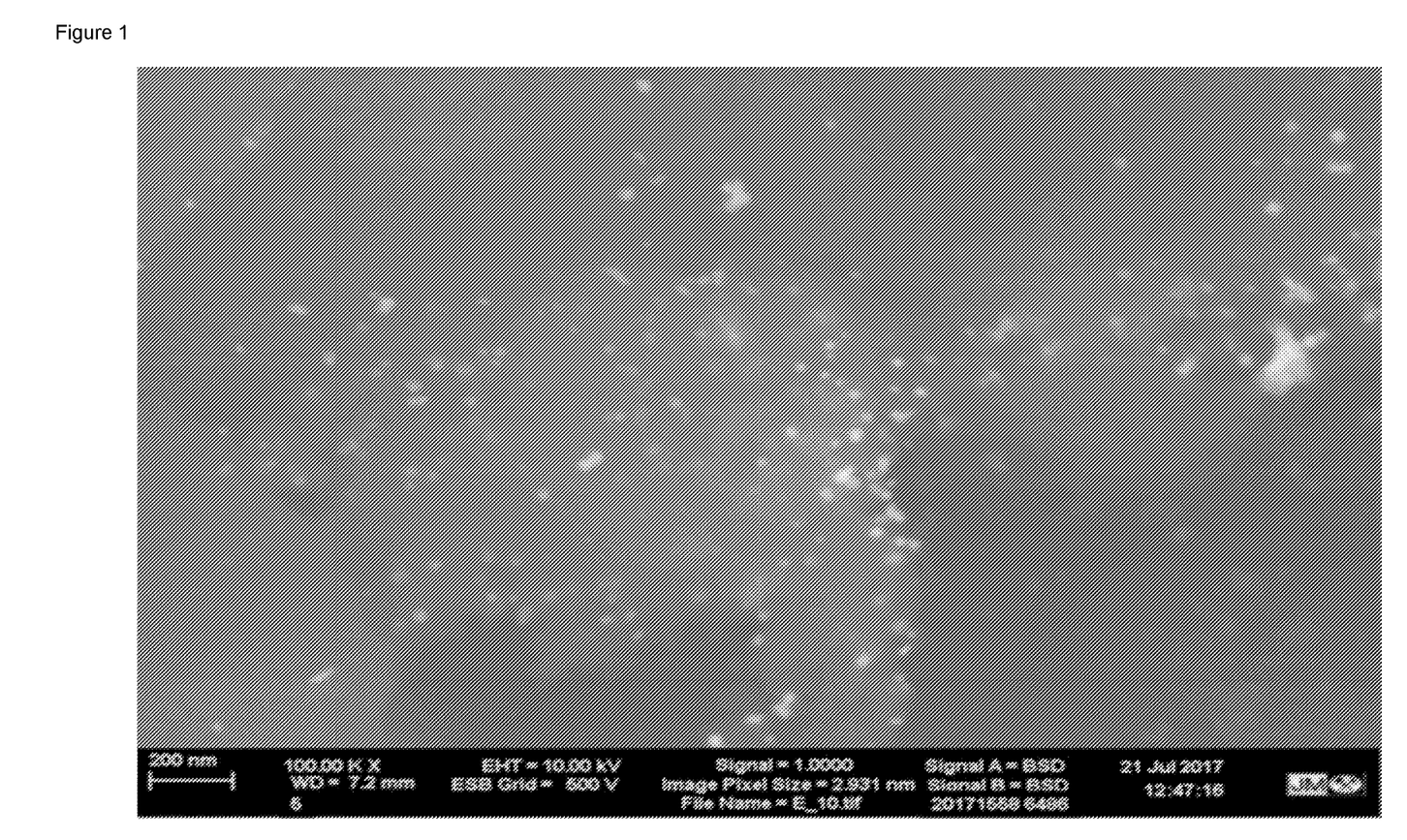
FIG. 1 is an SEM image of a fresh untreated 0.1% gold containing catalyst surface.

Example 1 (Comparative). Preparation of a 0.1% Au Thiosulphate Catalyst According to the Prior Art 0.142 g of an $HAuCl_4$ solution containing 41% Au was diluted in 24 ml of water. Separately, 0.186 g of anhydrous sodium thiosulphate was dissolved in 24 ml of water. The gold-containing solution was then added to the thiosulphate solution with stirring, to give a pale yellow mixed solution of prepared gold complex. 4.8 ml of this gold complex solution was then added to 5.8 g of commercially available activated carbon pellets, with stirring. The carbon absorbed all the liquid within about 5 minutes. After leaving the product to air-dry for about one hour, the material was then dried at 120° C. overnight, to give a catalyst containing approximately 0.1% Au. FIG. 1 is an SEM image of this freshly prepared untreated catalyst.

Example 2. Test for Carbon Nanotube Formation 5 g of the catalyst prepared as in example 1, was loaded into a 2 cm diameter stainless steel tube, and the bed formed supported at either end with silica wool packing. The tube was then placed in a tube furnace. A mixture of HCl and $C_2H_2$ (molar ratio 1.2:1) was passed over the catalyst at a flow rate of 240 ml/min, at a temperature of 220° C. Initial conversion to VCM was about 90%, falling to 65% after 48 hours. After 48 hours, the catalyst was flushed with nitrogen, cooled, and then removed from the furnace. Optical examination showed the presence of carbon nanotubes on the carbon pellets. The degree of nanotube formation was assessed as follows: 0=no nanotubes present; 1=nanotubes present on some particles; 2=nanotubes present on many particles; 3=nanotubes present on most particles.

Figure 3:
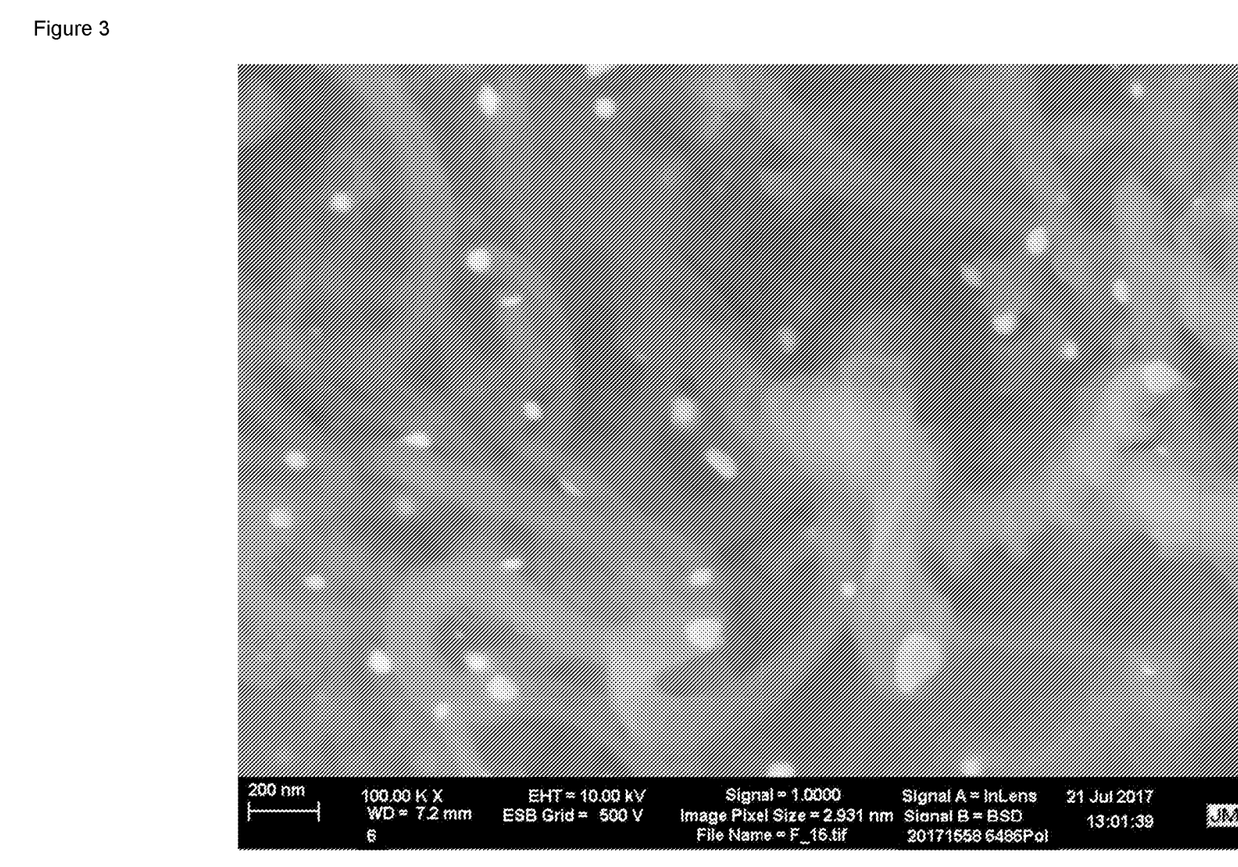
FIG. 3 is an SEM image of nanotube formation on the used untreated 0.1% gold containing catalyst surface.

SEM examination showed the coating to consist of a mass of carbon nanotubes, each nucleated by a gold particle as shown in FIG. 3. The degree of nanotube formation for this example was 3.

Example 3. Preparation of a Catalyst According to the Present Invention

The catalyst was prepared as in example 1, except that 0.58 g of an additive in the form of sodium metasilicate pentahydrate was dissolved in the $HAuCl_4$ solution. Thereafter the procedure was the same as for example 1.

Example 4. Preparation of a Catalyst According to the Present Invention

The catalyst was prepared as in example 1, except that 0.58 g of an additive in the form of sodium tetraborate was dissolved in the $HAuCl_4$ solution. Thereafter the procedure was the same as for example 1.

Example 5. Preparation of a Catalyst According to the Present Invention

Figure 2:
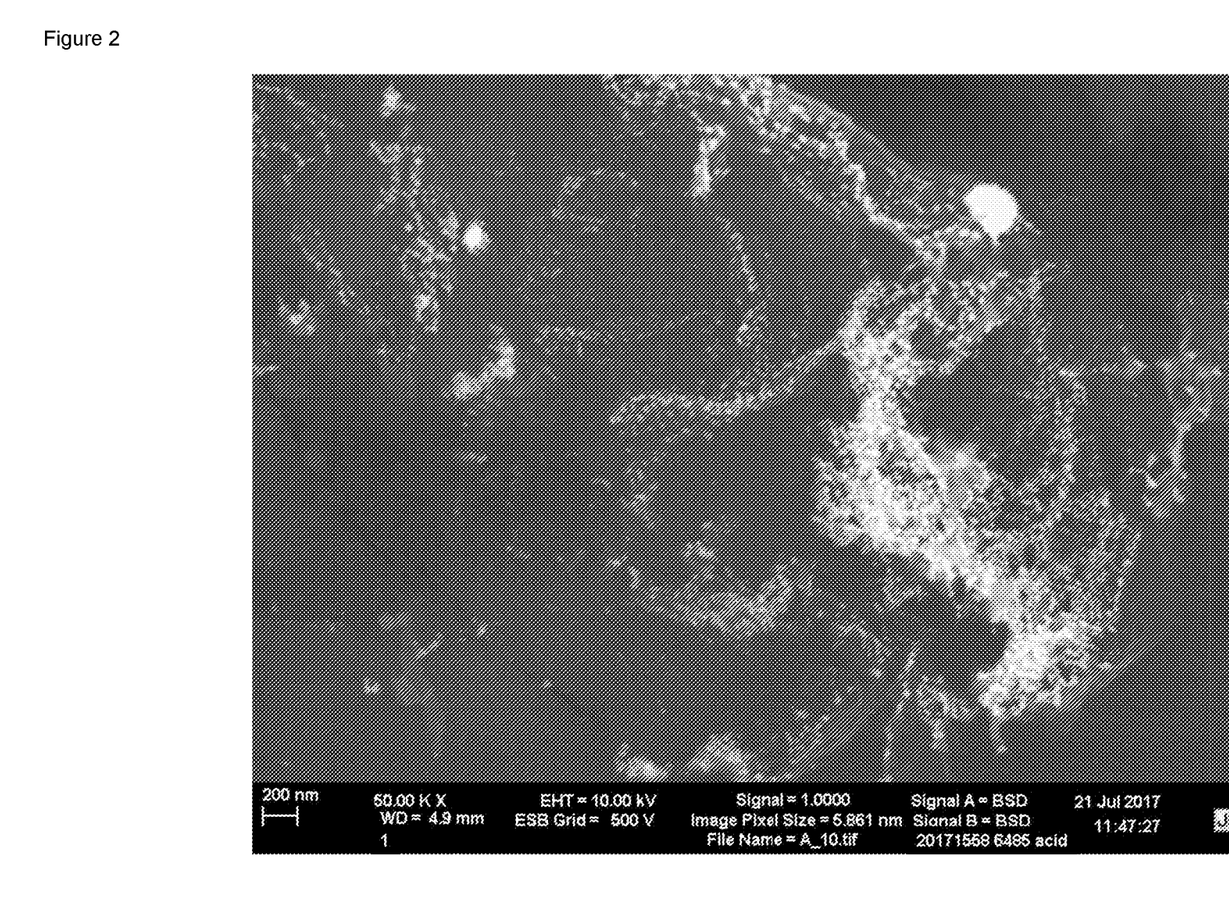
FIG. 2 is an SEM image of a fresh 1% boric acid treated 0.1% gold containing catalyst surface.

The catalyst was prepared as in example 1, except that 0.58 g of boric acid was dissolved in the $HAuCl_4$ solution. Thereafter the procedure was the same as for example 1. FIG. 2 is an SEM image of this fresh boric acid treated catalyst.

Example 6. Preparation of a Catalyst According to the Invention

The catalyst was prepared as in example 1, except that 0.58 g of trisodium orthophosphate was dissolved in the $HAuCl_4$ solution. Thereafter the procedure was the same as for example 1.

Figure 4:
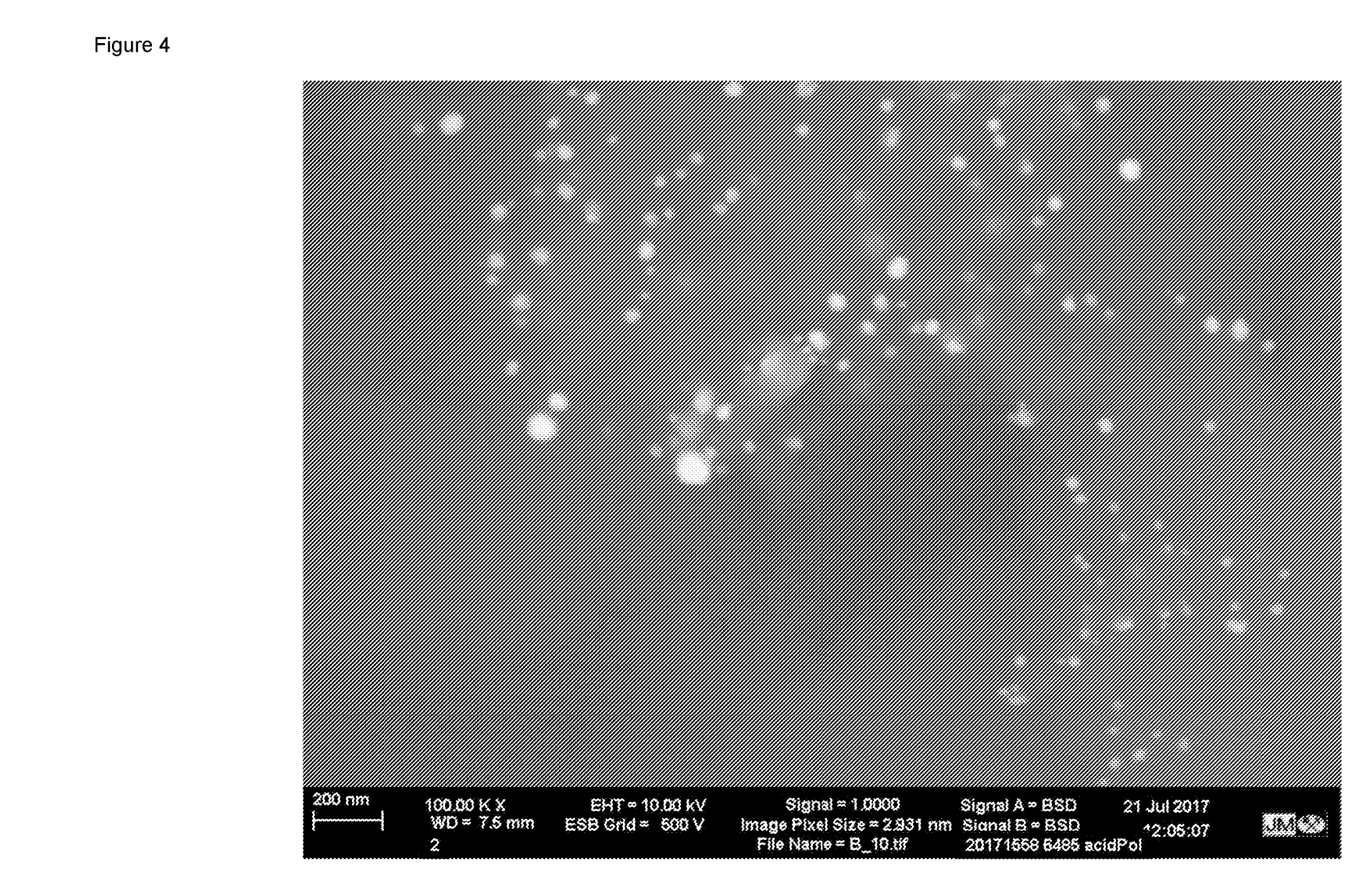
FIG. 4 is an SEM image of the used 1% boric acid treated 0.1% gold containing catalyst devoid of nanocarbon tube formation.

Example 7. Testing of Catalysts According to the Invention for Nanotube Formation Catalysts prepared as in examples 3-6 were tested for nanotube formation, according to the method given in Example 2, for time periods ranging from two to five days. In all cases carbon nanotube formation was either completely prevented (degree of nanotube formation=0) or present only on a few microscopic areas of the pellets (degree of nanotube formation=1). FIG. 4 is an SEM image of the boric acid treated catalyst of Example 5, after testing in accordance with the method of Example 2; here it can be seen that there is an increase in gold particle size, but no discernible nanotube growth. The degree of nanotube formation for this example was 0.

Example 8 (Comparative). Preparation of a 0.05% Au Catalyst According to the Prior Art The catalyst was prepared as in example 1, except that 0.071 g of an $HAuCl_4$ solution containing 41% Au was used to prepare the diluted $HAuCl_4$ solution; and 0.093 g of sodium thiosulphate was used to prepare the thiosulphate solution. The resulting catalyst contained approximately 0.05% Au.

Example 9. Preparation of an 0.05% Au Catalyst According to the Present Invention The catalyst was prepared as in example 8, except that 0.58 g of sodium metasilicate pentahydrate was dissolved in the $HAuCl_4$ solution. Thereafter the procedure was the same as for example 8.

Example 10. Testing of 0.05% Au Catalyst According to the Present Invention for Increased Activity The 0.05% Au catalyst with the silicate additive, according to Example 9, was subjected to the conversion test described in example 2. The rates of conversion are shown in FIG. 6, where it can be seen that a significant increase in conversion to VCM was obtained by the catalyst containing the silicate, versus the catalyst in which no silicate is present. For the material prepared in Example 9, nanotube formation was absent after six days, as can be seen in FIG. 5.

Figure 5:
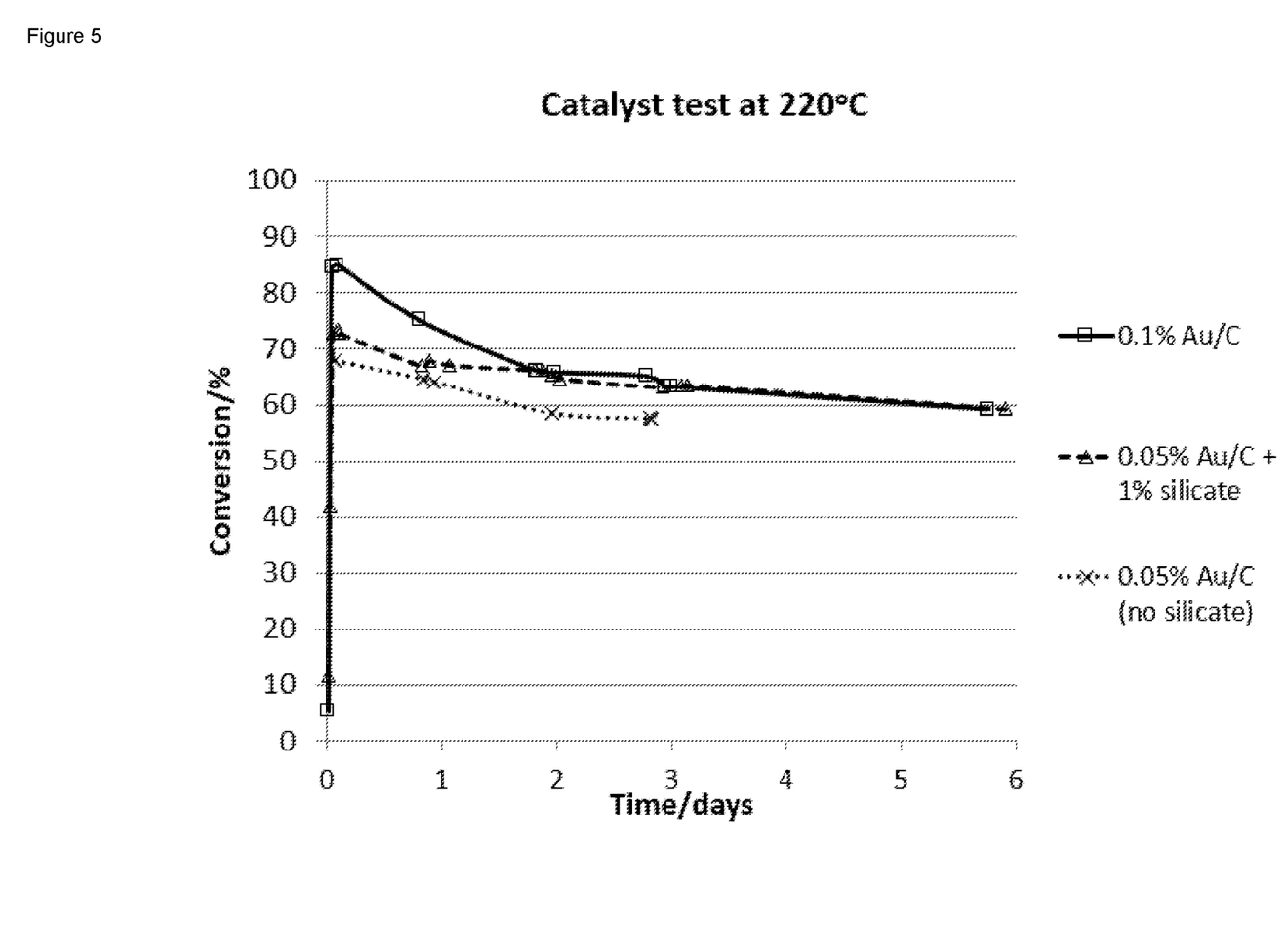
FIG. 5 illustrates the relative conversion rates to VCM obtained for untreated 0.1 and 0.05% gold containing catalysts versus a 0.05% gold containing catalyst treated with the addition of sodium silicate.
Figure 6:
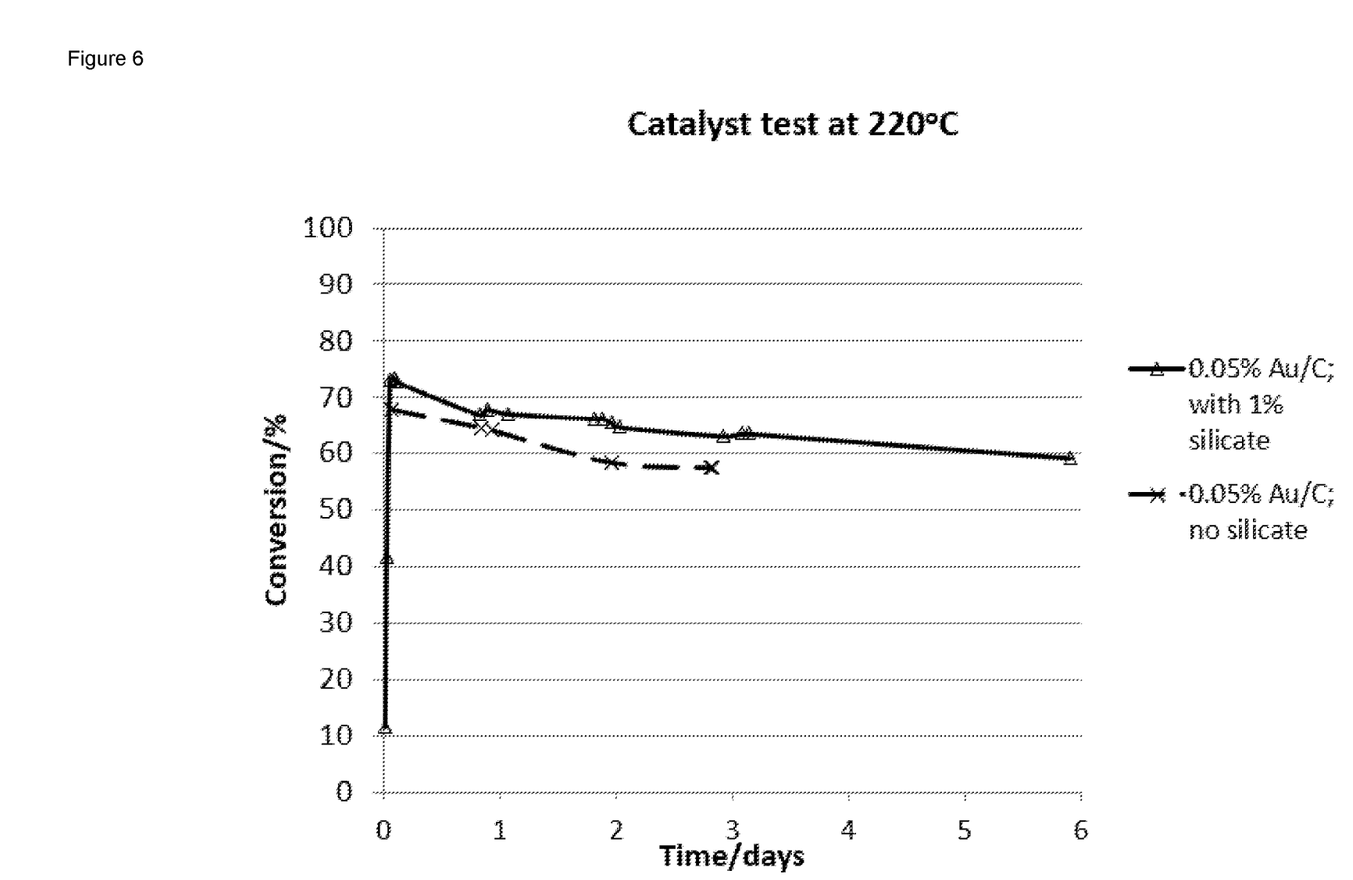
FIG. 6 illustrates a significant increase in VCM conversion obtained by a 0.05% gold containing catalyst with the addition of a silicate salt versus a gold containing catalyst in the absence of such a silicate salt.

FIG. 5 shows the rate of conversion to VCM at 220° C. as per Example 2, but over a longer time period (up to 6 days, opposed to 48 hours) for two untreated catalysts, one containing 0.1% Au, and the other 0.05% Au, as compared to the 0.05% Au when treated withسسsodium silicate addition, as described above. In FIG. 5 it can be clearly seen that the addition of the sodium silicate allows the lower 0.05% Au containing catalyst to achieve a selectivity comparable to the higher 0.1% Au containing (but untreated) catalyst.

The improvement in conversion demonstrated in Example 10 for a 0.05% Au and silicate containing catalyst does not apparently occur for an 0.1% Au catalyst, although nanotube formation is advantageously inhibited. Therefore, the present invention is particularly suited and desirable in catalysts which have less than 0.1% gold.

Examples 11-17

A solution of $HAuCl_4$ containing 0.100 g Au was diluted with the amount of demineralised water (DI) indicated. Separately, solutions of the sulfur-containing ligand and the additive were prepared with the amount of demineralised water (DI) indicated. The solutions were combined in the order indicated to produce a gold containing impregnation solution. This solution was then added to 100 g (dry weight) commercially available activated carbon pellets, via the incipient wetness technique, with mixing. The impregnated material was left to stand for approximately 30 minutes, during which all the added solution was adsorbed. The material was then dried at 105° C. overnight to give a catalyst containing approximately 0.1% Au.

In the case of Example 17, pH adjustment was carried out as follows. A solution of $HAuCl_4$ containing 0.100 g Au was diluted with 30 ml of demineralised water. A ca. 5% KOH solution was prepared by dissolving 5 g NaOH in 100 ml demineralised water. Approximately 1 ml of the KOH solution was added dropwise to the gold containing solution to form a solution having a pH of ca. 6.8. Separately 0.336 g ammonium thiosulphate was dissolved in 30 ml demineralised water. The gold-containing solution was then added to the ammonium thiosulphate solution with stirring, to give a mixed solution of prepared gold complex. The resulting solution was then used in the incipient wetness technique according to the above procedure.

XPS analysis of examples 11-16 indicated the presence of $SiO_2$ in the material formed following drying at 105° C. overnight.

The catalysts were tested for carbon nanotube formation according to the procedure in Example 2.

approximately 0.1% Au. This catalyst was tested as in Example 2. The degree of carbon nanotube formation was 1.

Example 19

0.1% Au/C catalyst was prepared was prepared as in example 18. Separately, 1.467 g zirconyl oxynitrate dihydrate $[ZrO(NO_3)_2.2H_2O]$ was dissolved in 30 ml demineralised water and this solution was added to 50 g of the dried gold containing carbon pellets via the incipient wetness impregnation technique. After leaving the material to stand for approximately 30 minutes, the material was dried at 105° C. overnight, to give a catalyst containing ca. 0.1% Au and 1% Zr.

Example 20

0.1% Au/C catalyst was prepared was prepared as in example 18. Separately 1.550 g cerium nitrate hexahydrate

TABLE 1

| Example | HAuCl4 solution [HAuCl$_4$] | Ligand solution [Ligand] | Additive solution [Additive] | Order of addition to form impregnation solution | pH adjustment | Degree of nanotube formation |
|---|---|---|---|---|---|---|
| 11 | 0.100 g HAuCl$_4$ in 12 mL DI | 0.373 g sodium thiosulphate in 24 mL DI | 1.162 g sodium metasilicate pentahydrate in 24 mL DI | [HAuCl$_4$] to [Ligand] then add [Additive] | –None | 0 |
| 12 | 0.100 g HAuCl$_4$ in 12 mL DI | 0.372 g sodium thiosulphate in 24 mL DI | 1.161 g sodium metasilicate pentahydrate in 24 mL DI | [HAuCl$_4$] to [Additive] then add [Ligand] | –None | 0 |
| 13 (Comparative) | 0.100 g HAuCl$_4$ in 30 mL DI | — | 1.160 g sodium metasilicate pentahydrate in 30 mL DI | [HAuCl$_4$] to [Additive] | None | 3 |
| 14 | 0.100 g HAuCl$_4$ in 12 mL DI | 0.200 g sodium thiocyanate in 24 mL DI | 1.162 g sodium metasilicate pentahydrate in 24 mL DI | [HAuCl$_4$] to [Ligand] then add [Additive] | None | — |
| 15 | 0.100 g HAuCl$_4$ in 12 mL DI | 0.200 g sodium thiocyanate in 24 mL DI | 1.162 g sodium metasilicate pentahydrate in 24 mL DI | [HAuCl$_4$] to [Additive] then add [Ligand] | None | 3 |
| 16 | 0.100 g HAuCl$_4$ in 12 mL DI | 0.180 g thiourea in 24 mL DI | 0.350 g silicic acid in 24 mL DI | [HAuCl$_4$] to [Ligand] then add [Additive] | None | 1 |
| 17 (Comparative) | 0.100 g HAuCl$_4$ in 30 mL DI | 0.336 g ammonium thiosulphate in 30 mL DI | — | [HAuCl$_4$] to [Ligand] | [HAuCl$_4$] adjusted to pH 6.8 using 1M KOH | — |

Zr, Ce and La Precursors

Example 18 (Comparative)

A solution of $HAuCl_4$ containing 0.100 g Au was diluted with 12 ml of demineralised water. A ca. 1M NaOH solution was prepared by dissolving 4 g NaOH in 100 ml demineralised water. 1.60 g of the prepared 1M NaOH solution was added dropwise to the gold containing solution to form solution having a pH of ca. 6.5. Separately 0.336 g sodium thiosulphate was dissolved in 12 ml demineralised water. The gold-containing solution was then added to the sodium thiosulphate solution with stirring, to give a mixed solution of prepared gold complex, having a pH of ca. 11.2. A further 12 ml of the previously prepared 1M NaOH solution and 22 ml demineralised water were added to the gold containing solution to give a solution of the prepared gold complex, having a pH of ca. 12.3. The resultant gold containing solution was then added to 100 g (dry weight) commercially available activated carbon pellets, via the incipient wetness technique, with mixing. The impregnated material was left to stand for approximately 30 minutes, during which all the added solution was adsorbed. The material was then dried at 105° C. overnight to give an Au/C catalyst containing $[Ce(NO_3)_3.6H_2O]$ was dissolved in 30 ml demineralised water and this solution was added to 50 g of the dried gold containing carbon pellets via the incipient wetness impregnation technique. After leaving the material to stand for approximately 30 minutes, the material was dried at 105° C. overnight, to give a catalyst containing ca. 0.1% Au and 1% Ce. This catalyst was tested as in Example 2. The degree of carbon nanotube formation was 1.

Example 21

0.1% Au/C catalyst was prepared was prepared as in example 18. Separately 1.335 g lanthanum chloride heptahydrate $[LaCl_3.7H_2O]$ was dissolved in 30 ml demineralised water and this solution was added to 50 g of the dried gold containing carbon pellets via the incipient wetness impregnation technique. After leaving the material to stand for approximately 30 minutes, the material was dried at 105° C. overnight, to give a catalyst containing ca. 0.1% Au and 1% La.

It will be appreciated by persons skilled in the art that the above embodiments have been described by way of example only, and not in any limitative sense, and that various alterations and modifications are possible without departure from the scope of the invention as defined by the appended claims.

The invention also includes the following embodiments:
1. A catalyst comprising a complex of gold with a sulphur-containing ligand and inorganic salt or acid on a support.
2. A catalyst according to embodiment 1, comprising between 10 and 0.1% inorganic salt or acid, by weight based on the total weight of the catalyst.
3. A catalyst according to embodiment 1, comprising between 5 and 0.1% inorganic salt or acid, by weight based on the total weight of the catalyst.
4. A catalyst according to embodiment 1, comprising between 3 and 0.5% inorganic salt or acid, by weight based on the total weight of the catalyst.
5. A catalyst according to any preceding embodiment, wherein the inorganic acid or salt is an inorganic acid selected from a boric acid, phosphoric acid or sulphuric acid.
6. A catalyst according to any one of embodiments 1 to 4, wherein the inorganic acid or salt is an inorganic salt selected from an ammonium, silicate, borate or phosphate salt.
7. A catalyst according to embodiment 6, wherein the inorganic salt is a sodium silicate, sodium borate or sodium phosphate salt.
8. A catalyst according to embodiment 7, wherein the inorganic salt is selected from sodium metasilicate pentahydrate, sodium tetraborate, boric acid, and trisodium orthophosphate.
9. A catalyst according to embodiment 6, wherein the inorganic salt is an ammonium salt.
10. A catalyst according to any preceding embodiment, comprising less than 1.0% of gold, by weight based on the total weight of the total catalyst.
11. A catalyst according to any preceding embodiment, comprising no more than 0.1% of gold, by weight based on the total weight of the total catalyst.
12. A catalyst according to any preceding embodiment, comprising no more than 0.05% of gold, by weight based on the total weight of the catalyst.
13. A catalyst according to any preceding embodiment, wherein said support comprises carbon.
14. A catalyst according to any preceding embodiments, wherein said support is in the form of a powder, granulate or shaped unit.
15. A catalyst according to any preceding embodiment, wherein at least some of the gold is in a positive oxidation state.
16. A catalyst according to any preceding embodiment, wherein said sulphur-containing ligand is an oxidising ligand containing sulphur in a positive oxidation state.
17. A catalyst according to embodiment 16, wherein said sulphur-containing ligand is selected from the group consisting of a sulphonate, thiosulphate, thiocyanate, thiourea, thionyl chloride, thiopropionic acid and thiomalic acid.
18. A catalyst according to any preceding embodiment, comprising sulphur in the range from about 0.005 to 15% by weight based on the total weight of the total catalyst.
19. A catalyst according to any preceding embodiment, further comprising a metal or a compound of a metal selected from the group consisting of cobalt, copper, lanthanum, cerium, lithium, sodium, potassium, rubidium, caesium, magnesium, calcium, strontium and barium.
20. A method of manufacturing a catalyst according to anyone of embodiments 1 to 19, wherein,
    i) a solution of gold is provided,
    ii) a solution of sulphur containing ligand is provided,
    iii) a solution of an inorganic salt or acid is provided,
    iv) the gold solution is mixed with the sulphur containing ligand solution to provide a gold complex impregnation solution,
    v) a catalyst support is impregnated with the gold complex impregnation solution, followed by drying the impregnated support,
    vi) the catalyst support is impregnated with the inorganic salt or acid, followed by drying the impregnated support.
21. A method of manufacturing a catalyst according to any one of embodiments 1 to 19, characterised in that,
    i) a solution of gold is provided,
    ii) a solution of sulphur-containing ligand is provided,
    iii) an inorganic salt or acid is added to either the solution of gold, or the solution of sulphur-containing ligand, prior to step iv)
    iv) the gold solution is mixed with the sulphur-containing ligand solution, wherein either the gold or sulphur-containing ligand solution also comprises the inorganic salt or acid, to provide a gold complex and inorganic salt or acid containing impregnation solution,
    v) a catalyst support is impregnated with the gold complex and inorganic salt or acid containing impregnation solution, followed by drying the impregnated support.
22. A method in accordance with embodiment 20 or 21, wherein the inorganic salt or acid is derived from a precursor which has been transformed.
23. A method in accordance with embodiment 22 where the precursor is transformed via a thermal or chemical degradation.
24. A method in accordance with any one of embodiments 20 to 23, further comprising an activation step.
25. A chemical process comprising reacting at least one chemical substrate in the presence of a catalyst according to any one of embodiments 1 to 19, or made by a process according to embodiment 20 or 21.
26. A chemical process according to embodiment 23, comprising the oxidation of said chemical substrate.
27. A process for the hydrochlorination of an alkyne comprising reacting said alkyne with hydrogen chloride in the presence of a catalyst according to any one of embodiments 1 to 19.
28. A process for the hydrochlorination of an alkyne, according to embodiment 25, comprising a step of treating said catalyst with hydrogen chloride in the absence of acetylene.

The invention claimed is:
1. A catalyst comprising:
    a complex of gold with a sulphur-containing ligand; and
    an additive that is an oxide, hydroxide, oxo-salt, or oxo-acid of silicon;
    on a support comprising carbon,
wherein the catalyst contains less than 0.5% of gold by weight based on the total weight of the catalyst; and,
wherein the catalyst has a silicon content of 0.1-10 wt % based on the total weight of the catalyst.
2. The catalyst according to claim 1, wherein the additive is a silicic acid.
3. The catalyst according to claim 1, wherein the additive is sodium metasilicate pentahydrate.

4. The catalyst according to claim 1, comprising no more than 0.1% of gold, by weight based on the total weight of the total catalyst.

5. The catalyst according to claim 1, comprising no more than 0.05% of gold, by weight based on the total weight of the catalyst.

6. The catalyst according to claim 1, wherein said sulphur-containing ligand is selected from the group consisting of a sulphate, a sulphonate, a thiosulphate, a thiocyanate, a thiourea, a thiol or thionyl chloride.

7. A method of manufacturing a catalyst according to claim 1, wherein,
   i) a solution of gold is provided,
   ii) a solution of sulphur containing ligand is provided,
   iii) a solution of an additive that is an oxide, hydroxide, oxo-salt, or oxo-acid of silicon, or precursor thereof is provided,
   iv) the gold solution comprising carbon is mixed with the sulphur containing ligand solution to provide a gold complex impregnation solution, and
   v-i) a catalyst support comprising carbon is impregnated with the gold complex impregnation solution, followed by drying the impregnated support, then impregnated with the solution from (iii), followed by drying the impregnated support, or
   v-ii) a catalyst support is impregnated with the solution from step (iii), followed by drying then impregnated support, then impregnated with the gold complex impregnation solution, followed by drying the impregnated support.

8. A method of manufacturing a catalyst according to claim 1, wherein,
   i) an impregnation solution is provided comprising a gold complex and an additive that is an oxide, hydroxide, oxo-salt, or oxo-acid of silicon, or a precursor thereof;
   ii) a catalyst support comprising carbon is impregnated with the solution from step (i) to produce an impregnated support, followed by drying the impregnated support.

9. The method according to claim 7, wherein the additive precursor is transformed into an inorganic oxide, hydroxide, oxo-salt or oxo-acid via a thermal or chemical degradation.

10. The method according to claim 8, wherein the additive precursor is transformed into an inorganic oxide, hydroxide, oxo-salt or oxo-acid via a thermal or chemical degradation.

11. A process for the hydrochlorination of an alkyne comprising reacting said alkyne with hydrogen chloride in the presence of a catalyst according to claim 1.

* * * * *